United States Patent
Dysarz

(10) Patent No.: US 6,235,003 B1
(45) Date of Patent: *May 22, 2001

(54) INCLINED PLANE LATCHING DEVICE FOR A SPRING NEEDLE CANNULA AND A SPRING NEEDLE

(76) Inventor: Edward D. Dysarz, 18 Front St., Rockport, TX (US) 78382

( * ) Notice: Subject to any disclaimer, the term of this patent is extended or adjusted under 35 U.S.C. 154(b) by 0 days.

This patent is subject to a terminal disclaimer.

(21) Appl. No.: 09/415,251

(22) Filed: Oct. 12, 1999

(51) Int. Cl.$^7$ .................................................. A61M 5/32
(52) U.S. Cl. ........................ 604/195; 604/110; 604/164.12
(58) Field of Search .................................. 604/110, 192, 604/195, 197, 198, 162, 164.04, 164.08, 164.12, 165.01, 170.05, 240–243, 161

(56) References Cited

U.S. PATENT DOCUMENTS

| | | | |
|---|---|---|---|
| 3,306,290 | 2/1967 | Weltman | 604/197 |
| 4,392,859 | 7/1983 | Dent | 604/198 |
| 4,973,316 | 11/1990 | Dysarz | 604/195 |
| 4,978,343 | 12/1990 | Dysarz | 604/195 |
| 5,019,044 | 5/1991 | Tsao | 604/110 |
| 5,084,018 | 1/1992 | Tsao | 604/110 |
| 5,120,310 | 6/1992 | Shaw | 604/110 |
| 5,267,961 | 12/1993 | Shaw | 604/110 |
| 5,385,551 | 1/1995 | Shaw | 604/110 |
| 5,389,076 | 2/1995 | Shaw | 604/110 |
| 5,997,507 | * 12/1999 | Dysarz | 604/161 |

* cited by examiner

Primary Examiner—Anhtuan T. Nguyen

(57) ABSTRACT

A spring needle cannula with a first end and a second end wherein said first end is inserted into a body to inject medicament into said body and wherein the second end of said spring needle cannula is formed into a coiled spring and wherein said coiled spring is stretched into a biased spring needle cannula and contained in a modular hub chamber and wherein said first end of said spring needle cannula extends from a tunnel formed in said first end of said modular hub chamber and wherein said second end of said needle cannula is formed into a biased spring cannula and held between an inclined plane latching means and a flange, fixed to a ridge formed at the second end of said modular hub chamber. To release said biased spring needle cannula after said spring needle cannula has been used to inject medicament into a body, a button is depressed thus releasing the biased spring needle from said inclined plane latching means thereby releasing said biased spring needle allowing said biased spring needle cannula to form a coil near said second end of said hub chamber and thus retracting said first end of said needle into said modular hub chamber thereby rendering said needle harmless from an accidental needle prick. The inclined plane latching device may be used on a needle cannula or on a needle for an IV catheter.

6 Claims, 6 Drawing Sheets

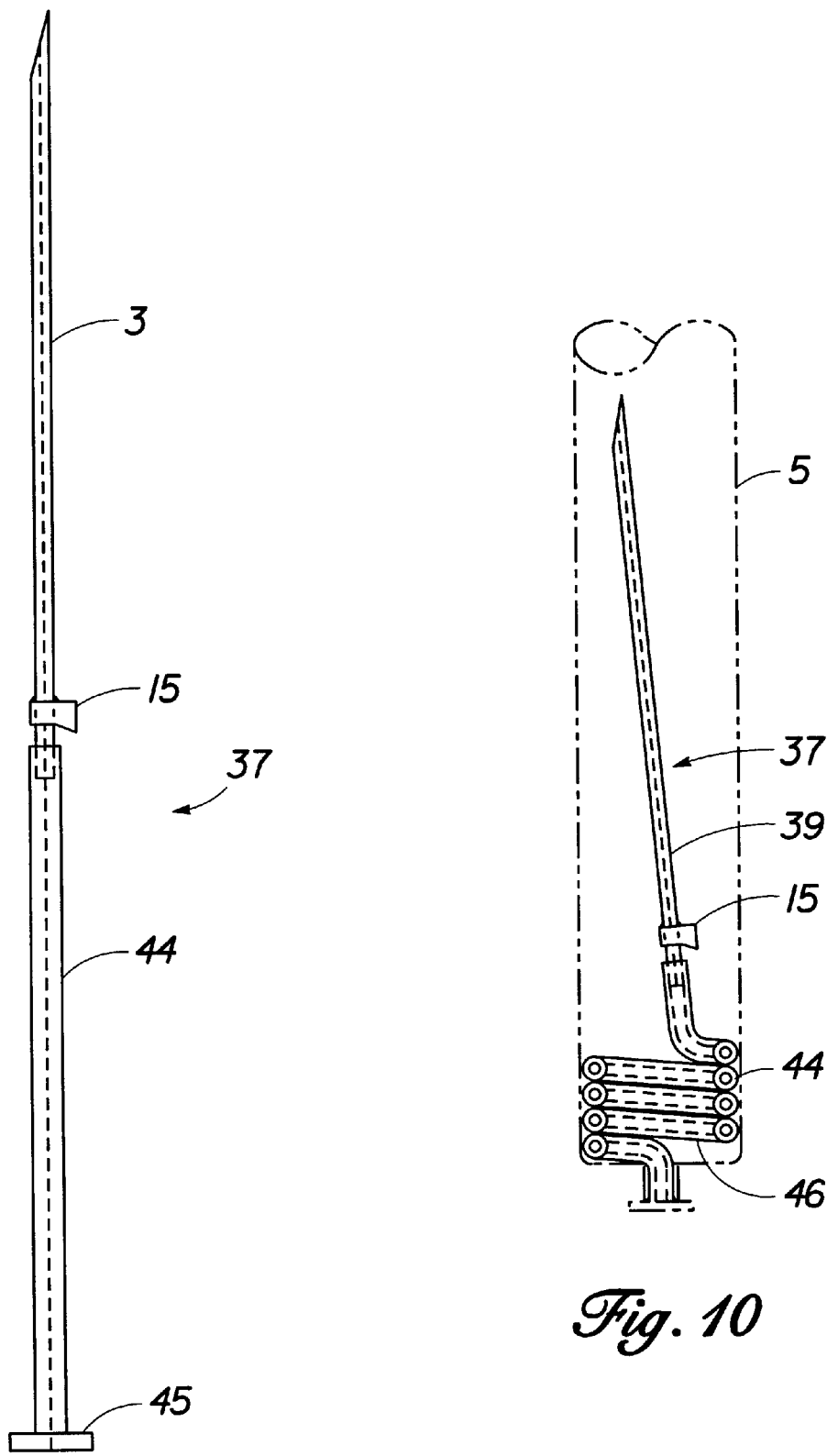

INCLINED PLANE LATCHING DEVICE FOR A SPRING NEEDLE CANNULA AND A SPRING NEEDLE

BACKGROUND OF THE INVENTION

There are many safety syringe designs available today. All of these designs that have various types of latching devices are Z. M. Roehr et al U.S. Pat. No. 3,008,570, Z. M. Roehr U.S. Pat. No. 3,107,785, Bartner, et al U.S. Pat. No. 3,895,633, G K Burke U.S. Pat. No. 3,306,291, Gyure et al U.S. Pat. No. 4,300,678, Winstead Hall U.S. Pat. No. 6,356,822, Sampson U.S. Pat. No. 4,425,120, Larson U.S. Pat. No. 4,639,249, Harbaugh U.S. Pat. No. 4,655,751, Strauss U.S. Pat. No. 4,664,654, Braginetz U.S. Pat. No. 466,435, Spencer U.S. Pat. No. 4,702,738, Milorad U.S. Pat. No. 4,702,739, Spencer U.S. Pat. No. 4,801,295, Poncy U.S. Pat. No. 4,815,022, and Hughes U.S. Pat. No. 4,840,619.

Other designs have a retractable needle such as Weltman U.S. Pat. No. 3,306,290, and Dent U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis, or other diseases from an accidental injection with a contaminated needle into others after the needle of the syringe has been inserted into a patient with the above mentioned diseases. These various designs all work well up to a degree, but they all fall short of their intended purpose during the act of covering the needle, or removing the needle, which requires two hands.

Other devices such as Tsao U.S. Pat. No. 5,019,044, Tsao U.S. Pat. No. 5,084,018, Shaw U.S. Pat. No. 5,267,961, Shaw U.S. Pat. No. 5,389,076, Shaw U.S. Pat. No. 5,385,551, Shaw U.S. Pat. No. 5,120,310, Dysarz U.S. Pat. No. 4,978,343, and Dysarz U.S. Pat. No. 4,973,316 are capable of releasing the needle cannula if the container that they are packaged in is dropped or jarred severely. These devices do not have a positive latching means but they rely on friction to restrain the needle cannula with the biased spring.

All of these designs also combine the needle cannula with the syringe and therefore create a storage problem. At present, needle cannulas are fixed to the hub but not to the syringe so that a variety of lengths and gauges of needle cannulas are stored in one locker or storage cabinet which may contain about twenty various lengths and gauges of needle cannulas; an inventory of about twenty or more of each gauges and lengths of needle cannulas may be stored in each section. There may also be about ten sizes of syringes with about twenty or more of each syringe stored in the same locker. When a given quantity of a given medicament is required, the proper size of needle cannula is fitted to the proper syringe thereby combining the right length and gauge of needle cannula with the right size of syringe.

All of the above inventions would require an inventory ten times of that of the present invention. Each needle cannula size would have to be fixed to each syringe size and each syringe size would have to be fixed to each needle cannula size and this would be hundreds of needle cannula syringe combinations which would be multiplied by ten each the numbers required for the necessary inventory in a given floor of a hospital would be astronomical. The need has developed for a safety needle cannula that would be a module apart from the syringe.

SUMMARY

It is the object of this invention is to provide a safe, dependable and a positive latch and release means for a needle cannula wherein the needle cannula that is used is independent of the syringe and is retracted into the module hub chamber and protects others from an accidental pricking after the needle cannula has been used, the needle can be retracted into the module hub chamber with the use of only one hand and that one hand being the hand that was used to inject the needle into the patient.

Another object of the present invention is to render the needle cannula useless after the needle cannula is retracted into the module hub chamber and to further prevent the reuse and abuse by users of illicit drugs.

It is still another object of the present invention to further prevent the accidental release of the needle cannula after the needle cannula is in the hub chamber.

It is still yet another object of the present invention to provide a safety needle cannula and a latch and release means without modifying the syringe.

The foregoing and other objects and advantages are attained by a spring needle cannula, a hub chamber, a hub to fix the device to a standard syringe, an inclined plane latching means and a latch release means wherein when said needle cannula is used to inject a drug, medicament, or other material into a body the latch release means is activated and the coiled spring cannula withdraws the distal end of said spring needle cannula into the hub chamber rendering the spring needle cannula harmless to prevent the accidental pricking of others and to prevent the contaminated spring needle cannula from being removed from the hub chamber.

The features of the present invention can be best understood together with further objects and advantages by reference to the following descriptions when taken in connection with accompanying drawings, wherein like numerals indicate like parts.

BRIEF DESCRIPTION OF THE DRAWINGS

FIG. 9 Is an elevation view of a composite spring needle cannula that is comprised of two tubes fixed together.

FIG. 10 Is a section elevation of the composite spring needle cannula retracted.

DETAILED DESCRIPTION OF THE PREFERRED EMBODIMENTS

Figure 1:
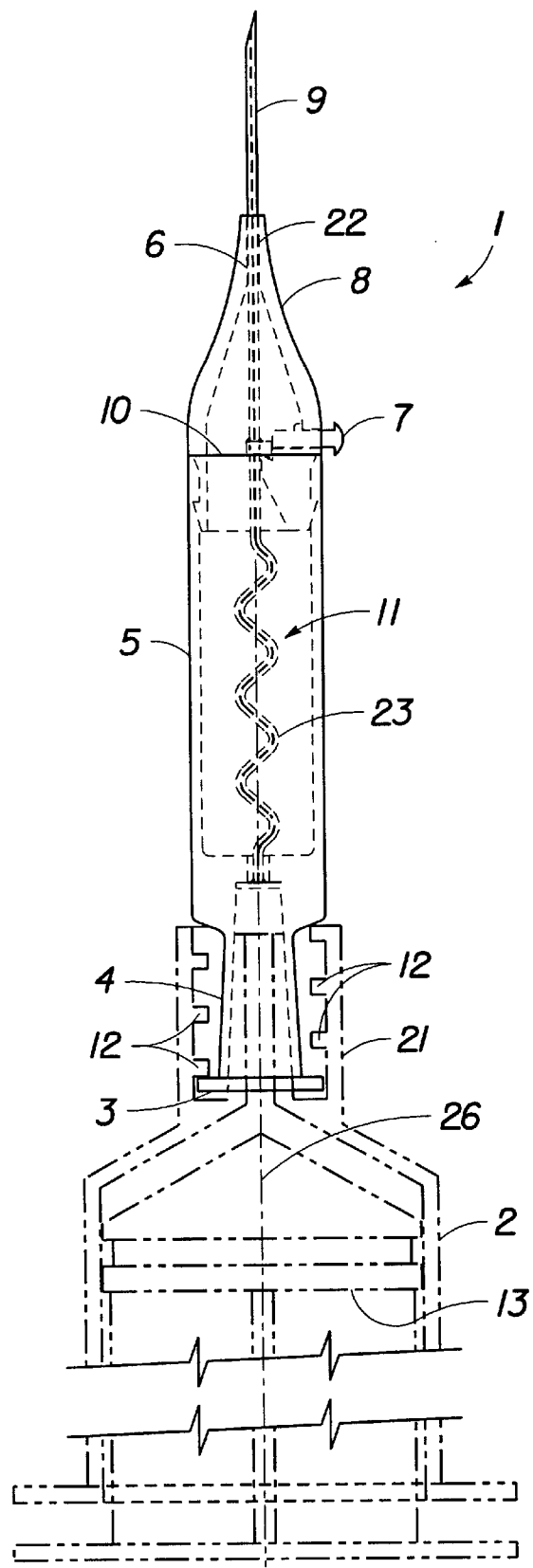
FIG. 1 Is an elevation view of the device fixed to the syringe.

Referring to FIG. 1 there is shown an elevation view if the modular assembly device 1 of the first preferred embodiment.

The modular assembly device 1 is shown as the first preferred embodiment, is a modular assembly suitably fixed to the threads 12 inside of the threaded extension 21 of a typical syringe 2 in a conventional manner. This type of threaded extension 21 is often referred to as a Lure-Lock tip however the tip could be a slip tip, an eccentric tip or a catheter tip by design choice. The threaded extension 21 is part of a typical or conventional syringe 2. The syringe 2 is shown with a plunger 13 for reference only. The modular assembly device 1 as shown is fixed to any conventional or typical syringe 2 without any modifications required to the syringe 2. The modular assembly device 1 will interface with any existing syringe by design choice.

The cannula distal end 9 is shown extending from the hub chamber cap tip 22 at the first end of the hub chamber cap 8, through the hub tunnel 6. The second end of the hub chamber cap 8 is shown suitably fixed to the first end of the hub chamber with a snap on the interface connection referred to as the hub joint 10. The cannula release button 7 is shown extending from the hub chamber cap 8, however, it could also be shown extending from the hub chamber by design choice. The spring needle cannula 11 distal end 9 extends into the hub chamber 5 wherein the spring needle cannula 11 is formed into coils 23.

The proximal end of the spring needle cannula 11 is shown suitably fixed to the first end of the hub 4. The first side of the threaded flange 3 is shown at the second end of the hub 4. The second side of the threaded flange is near the syringe 2. The threaded flange 3 is shown threaded or suitably fixed to the internal threads 12 that are on the inside of the threaded extension 21 that is at the first end of the syringe 2. A centerline 26 is shown that extends from the distal end of the spring needle cannula 11 to the second end of the syringe to transfer medicament from a syringe 2. The modular assembly device is used as a conduit to transfer medicament from a syringe 2 and dispose said medicament into a body.

Figure 2:
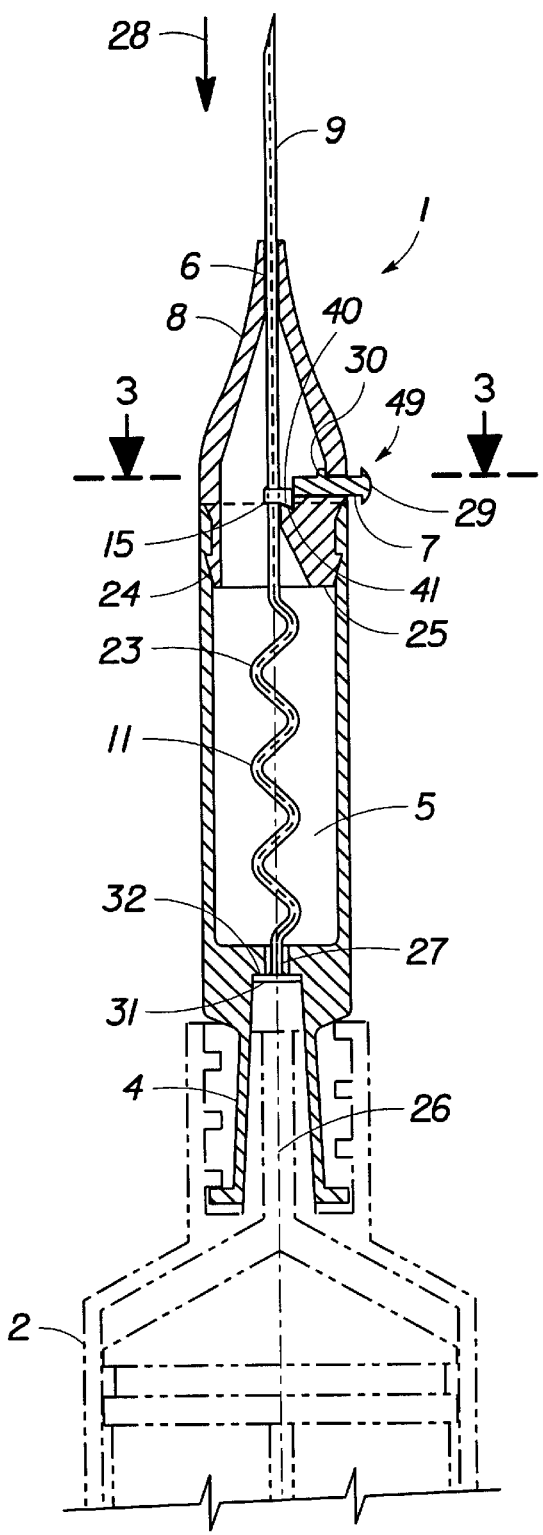
FIG. 2 Is an enlarged section elevation of the device fixed to a syringe.

Referring to FIG. 2 there is shown an enlarged section elevation of the modular assembly device 1 suitably fixed to the syringe 2. The cannula distal end 9 is shown extending from the hub tunnel 6 of the hub chamber 5. The hub chamber cap 8 is shown suitably fixed to the hub chamber 5 with a snap on connection 24 that could also use adhesive to make up the connection by design choice.

The latch release means 49 is shown as part of the hub chamber cap 8 how ever it could also be part of the hub chamber by design choice. The latch foundation 25 is shown formed on the inside of the hub chamber cap 8 and extends toward the centerline 26 of the device 1. A first inclined plane as shown formed on the latch foundation 25. Part of the cannula push out hook 15 is shown hooked onto the inclined plane latch 14. The cannula push out hook 15 is shown suitably fixed to the spring needle cannula 11 by adhesive or other suitable means. The spring needle cannula 11, is disposed in a hole formed in the cannula push out hook 15 wherein the hole extends from the first side to the second side of the cannula push out hook 15 wherein the spring needle cannula is disposed in the hole formed in the cannula push out hook 15. The third side of the cannula push out hook 15 is shown with a second inclined plane 41 that will correspond with the first inclined plane 40 of the catch and release means 49. The cannula push out hook 15 with the second inclined plane 41 formed at the second end of the cannula push out hook 15 is held in place in the first inclined plane 40 by the tension caused by the coils 23 or biased means formed near the proximal end 27 of the spring needle cannula 11. The coils 23 shown in FIGS. 1 and 2 are biased coils. The cannula push out hook 15 that is held in place in the latch foundation 25 further prevents the cannula distal end 9 from being thrust back 28 when the spring needle cannula 11 is inserted into a body.

The cannula release button 7 is shown near the incline plane latch 15 and is disposed in the hub chamber cap hole 33 formed in the hub chamber cap 8 that extends from the outside to the inside of the hub chamber 8. The cannula release button 7 is shown with a second knob 30 fixed to the third end of the cannula release button 7 to further prevent the cannula release button 7 from being removed or from falling out of the hub chamber cap hole 33 formed in the hub chamber cap 8 . The first knob 29 is shown at the first end of the cannula release button 7 wherein when the cannula release button 7 is depressed it will disengage the cannula push out hook 15 from the latch foundation 25.

A flange 31 is show suitably fixed to the proximal end 27 of the spring needle cannula 11 by welding, adhesive, or some other suitable means by design choice. The flange 31 is held in place in a ridge 32 formed on the inside of the second end of the hub chamber 5. The hub 4 is shown suitably attached to the syringe 2. The hub chamber 5 is integral with the hub 4. The hub 4 could also be a slip on hub by design choice.

Figure 3:
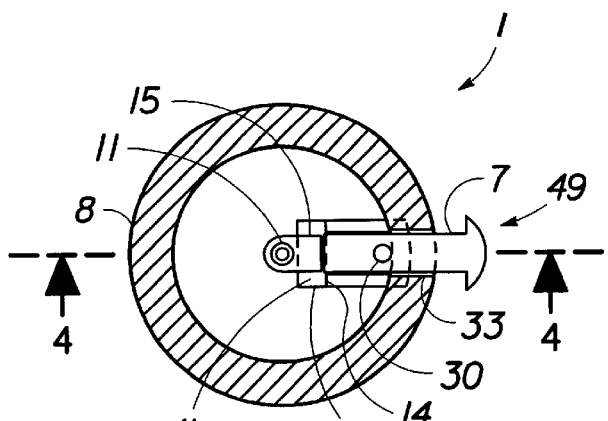
FIG. 3 Is an enlarged section elevation as taken through FIG. 2.

Referring to FIG. 3 there is shown a section elevation of the modular assembly device 1 and the latch and release means 49 as taken through FIG. 2.

The hub chamber cap 8 is shown with a hub chamber cap hole 33 wherein the cannula release button 7 is disposed in the hub chamber cap hole 33. The second end of the cannula release button 7 is shown near the third end of the cannula push out hook 15. The cannula push out hook 15 is further being held in place by the combination of the tension of the spring needle cannula 11 and first inclined plane of the cannula push out hook 15 suitably hooked to the second inclined plane 41 of the latch foundation 25 wherein the latch foundation 25 is shown near the cannula release button 7. The second knob 30 is seen on the cannula release button 7.

Figure 4:
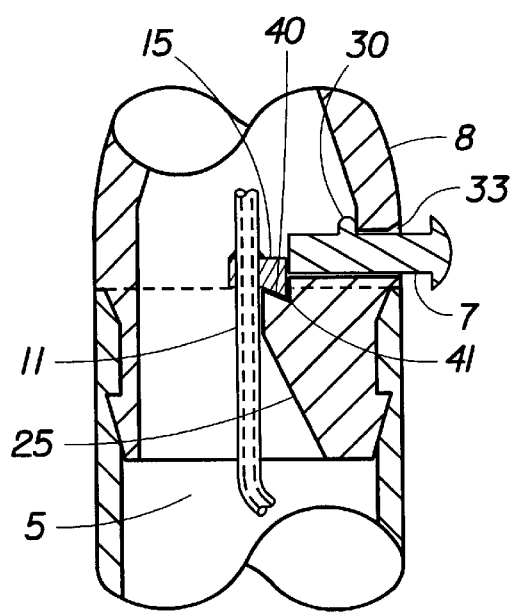
FIG. 4 Is a section elevation as taken through FIG. 3.

Referring to FIG. 4 there is shown an enlarged section elevation of the latch and release means 49 as taken through FIG. 3.

The cannula push out hook 15 with the first inclined plane 40 is shown securely held in the second inclined plane 41 that is formed in the latch foundation 25. To release the cannula push out hook 15 the cannula release button 7 must be pushed by a finger or thumb or by pressing the cannula release button into a hard object. The cannula push out hook 15 is restrained from moving out because the spring needle cannula 11 is pulling the cannula push out hook 15 into the second inclined plane 41 of the latch foundation. The cannula release button 7 is prevented from being pushed out of the hub chamber 5 or the hub chamber cap 8 by the second knob 30 that is pressing on the inside surface of the hub chamber cap 8.

The hub chamber cap hole 33 is shown formed in the hub chamber cap 8 wherein the hub chamber cap hole 33 extends from the inside surface to the outside surface of the hub chamber cap 8.

Figure 5:
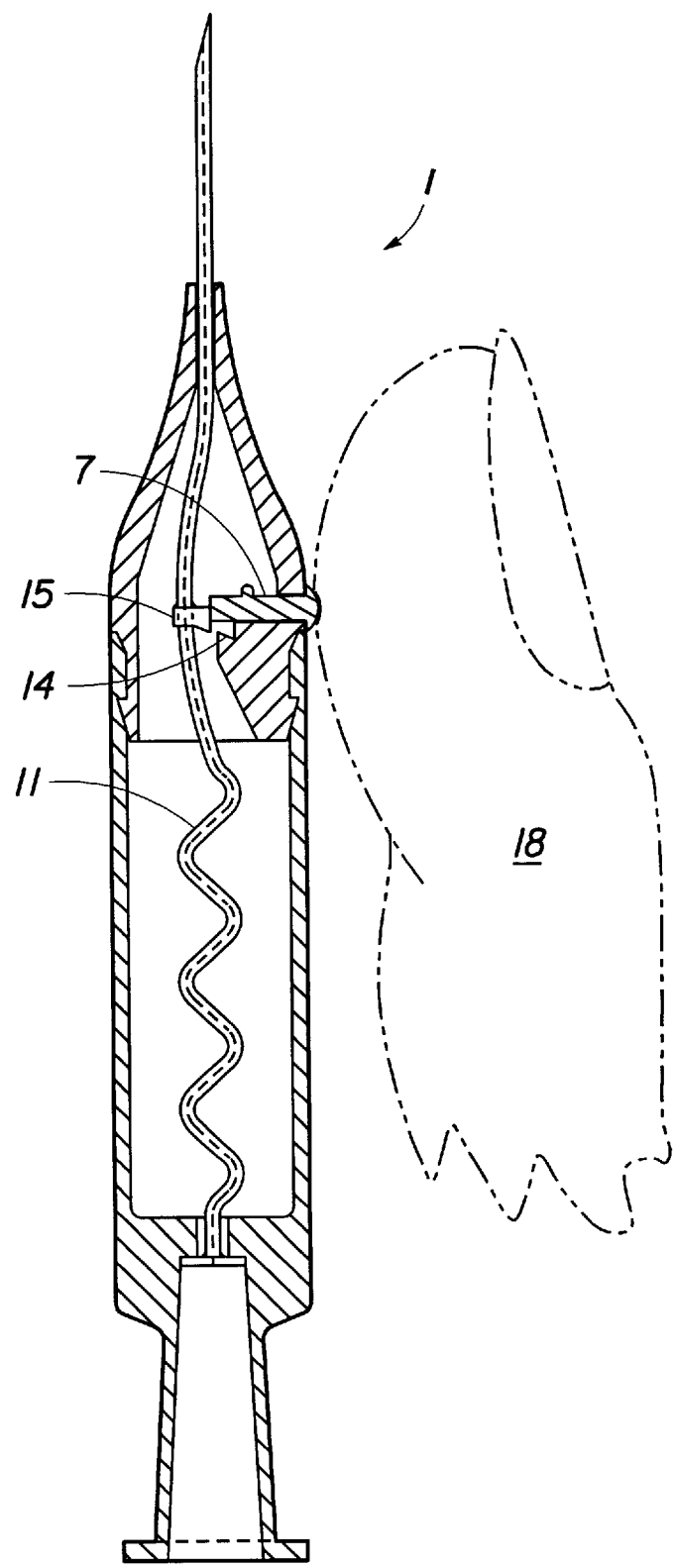
FIG. 5 Is a section elevation view of the latch and release means being disengaged.

Referring to FIG. 5 there is shown a section elevation view of the cannula push out hook 15 being released from the latch foundation 25.

The cannula release button 7 is shown being pushed by a finger 18 or a thumb wherein the second end of the cannula release button 7 pushes the cannula push out hook 15 out and away from the latch foundation 25. The spring needle cannula 11 is shown bending and is resisting the thrust of the cannula release button 7.

Although the syringe is not shown in FIG. 5 it should be assumed that the modular assembly device 1 is still fixed to the syringe as in FIG. 1 and FIG. 2 however, the operation to disarm or to release the spring needle cannula 11 could take place with the modular assembly device 1 fixed to the syringe or with the modular assembly device 1 removed from the syringe. The ability to release the spring needle cannula 11 does not in any way depend on the syringe.

Figure 6:
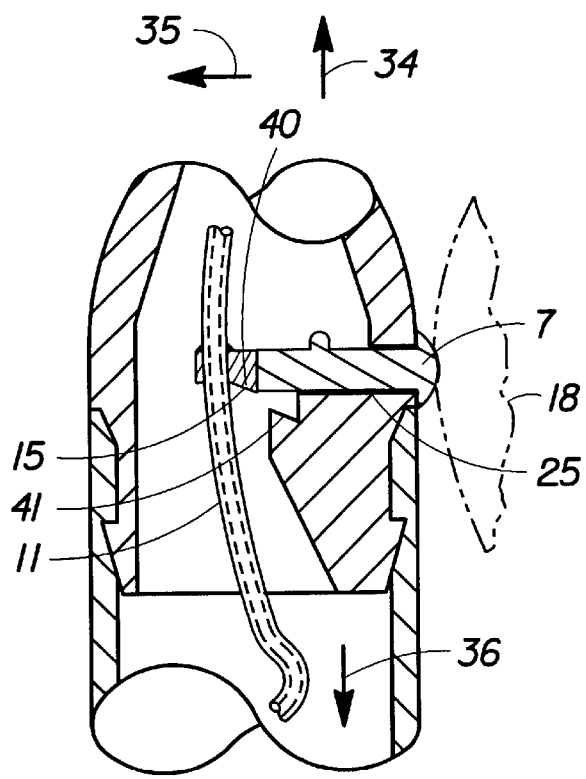
FIG. 6 Is an enlarged section elevation of the latch and release means being disengaged.

Referring to FIG. 6 there is shown an enlarged section elevation cannula push out hook 15 of the latch and release means 49 after the cannula push out hook 15 has been released from the latch foundation 25.

The cannula release button 7 is shown being pushed by a finger 18 or a thumb wherein the second end of the cannula release button 7 thrusts on the third end of the cannula push out hook 15 and thus pushes the cannula push out hook 15 out and away from the latch foundation 25.

As the cannula push out hook 15 is pushed away from the latch foundation 25 the cannula push out hook 15 moves some in the first end direction 34 due to the first incline plane 40 of the cannula push out hook 15 thrusting against the the second inclined plane 41 of the lath foundation 25. The cannula push out hook 15 also moves in the centerline direction 35 as the cannula release button thrusts on the cannula push out hook 15. The location of the cannula push out hook 15 relative to the latch foundation 25 as shown in FIG. 6 should last but a brief moment because the coils of the spring needle cannula 11 will instantly pull the cannula push out hook 15 in a hub direction 36. A damper could be added to the latch release means to slow the movement of the spring needle cannula by design choice.

Figure 7:
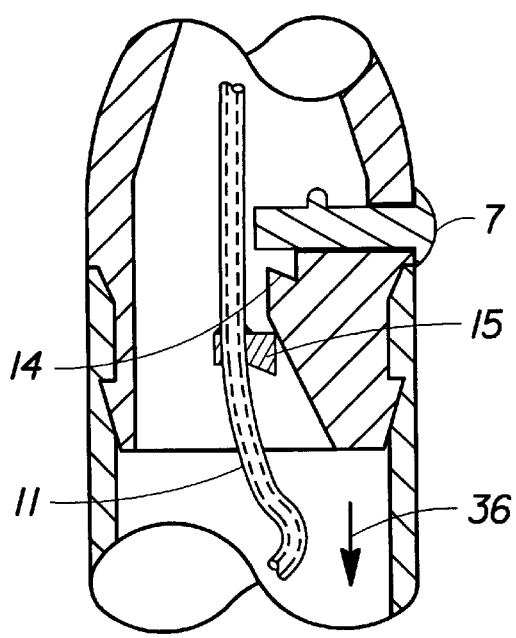
FIG. 7 Is an section elevation of the latch and release means disengaged

Referring to FIG. 7 there is shown a section elevation view of the cannula push out hook 15 and the spring needle cannula 11 moving in the hub direction 36.

The cannula release button 7 has pushed the cannula push out hook 15 past the second end of the latch foundation 25 and now the cannula push out hook 15 is being pulled in the hub direction 36 by the coil formed on the second end of the spring needle cannula 11.

This view is only going to last only an instant.

Figure 8:
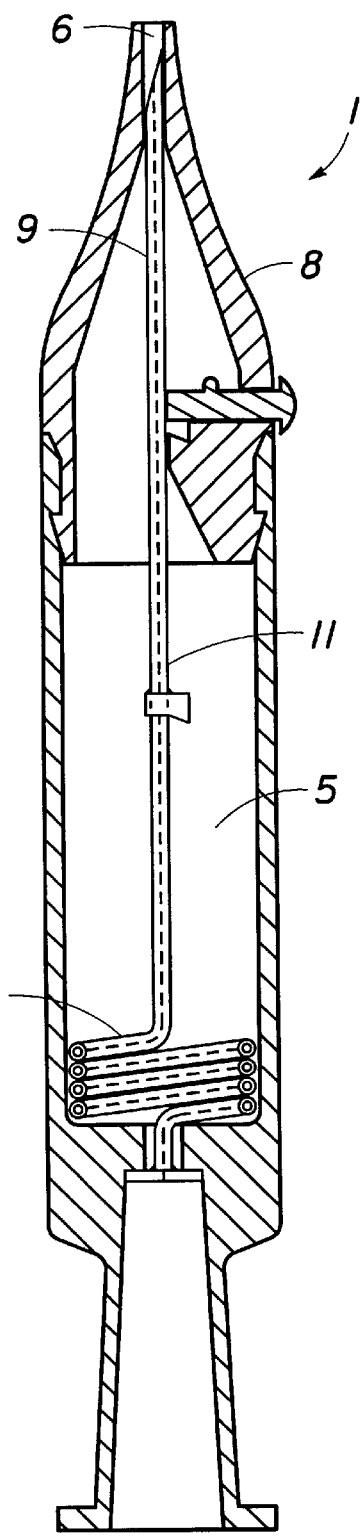
FIG. 8 Is a section elevation view of the device with the spring needle cannula contained in the hub chamber.
Figure 11:
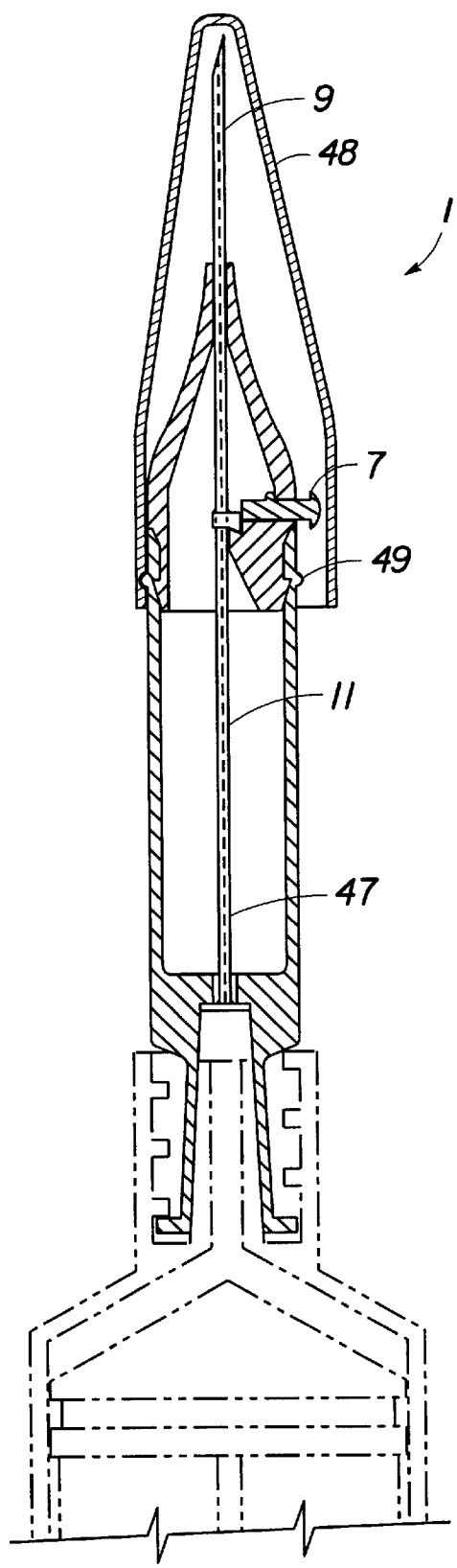
FIG. 11 Is a section elevation of a modular device wherein the spring needle cannula has been pulled into a straight or almost straight line.
Figure 12:
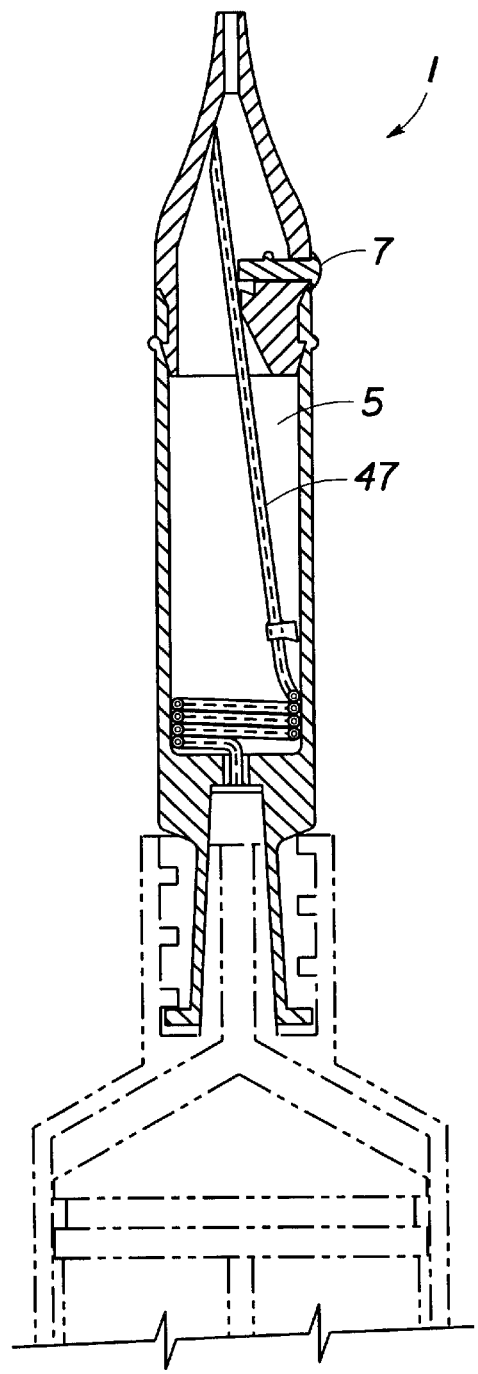
FIG. 12 Is a section elevation view of the spring needle cannula of FIG. 11 being retracted into the hub chamber.

Referring to FIG. 8 there is shown a section elevation of the modular assembly device 1 after the coils 23 have pulled the spring needle cannula 11 into the inside of the hub chamber 5, thus the needle cannula 11 is trapped in the modular hub chamber.

The cannula distal end 9 has been pulled into the hub tunnel 6, the hub chamber cap 8 and into the hub chamber 5 wherein it will be constantly held by the coils 23 and therefore will be prevented from extending past the hub tunnel 6 and will be unable to prick or otherwise injure anyone.

Referring to FIG. 9 there is shown an elevation veiw of a composite spring needle cannula 37.

The purpose of the composite spring needle cannula 37 is to allow for a greater diameter cannula in the area of the spring cannula 44 wherein the spring cannula 44 will not crimp durring the manufacturing and coiling process. Another purpose of the composite spring needle cannula 37 is to have one grade of steel for

What is claimed as invention is:

1. A latch and release means for latching and releasing a biased spring needle contained in a syringe or an IV catheter Comprised:

a hub chamber with a first end and a second end wherein said hub chamber is an elongated hollow tube;

a biased spring needle with a first end extending past said first end of said hub chamber and second end fixed near said second end of said hub chamber;

a cannula push out hook wherein said cannula push out hook is fixed to said spring needle and wherein said cannula push out hook has a first inclined plane formed at one end of said cannula push out hook;

a latch foundation wherein said latch foundation is formed on said hub chamber or fixed to said hub chamber and wherein said latch foundation has a second inclined plane formed on said latch foundation and wherein said second inclined plane is engaged with said first inclined plane formed on needle push out hook;

a cannula release button with a first end and second end wherein said second end of said cannula release button is near said cannula pushout hook and wherein said first end of said cannula release button is pushed thereby thrusting said cannula push out hook away from said latch foundation thereby disengaging said first inclined plane formed on said cannula push out hook from said second inclined plane formed on said latch foundation thereby allowing said second end of said spring needle to pull said first end of said spring needle into said hub chamber thereby preventing any reuse or accidental prick from said first end of said needle.

2. A latch and release means of claim 1 wherein said latch and release means may be used on an IV catheter.

3. A latch and release means of claim one wherein said latch and release means may be used on a syringe.

4. A latch and release means of claim 1 wherein said latch foundation is formed on a hub chamber cap.

5. A latch and release means of claim 1 wherein said cannula release button has a second knob formed near the second end of said cannula release button wherein said second knob prevents said cannula release button from falling out of said hub chamber.

6. The latch and release means of claim 1 wherein said cannula push out hook has a hole formed near said third end wherein said hole extends from said first to said second end of said cannula push out hook and wherein said needle is disposed in said hole.

\* \* \* \* \*